United States Patent [19]

Willenborg et al.

[11] Patent Number: 5,691,346
[45] Date of Patent: Nov. 25, 1997

[54] CASTANOSPERMINE AS AN ANTI-INFLAMMATORY AND IMMUNOSUPPRESSANT AGENT

[75] Inventors: David Otto Willenborg, Sterling; William Butler Cowden, Kambah; Christopher Richard Parish, Campbell, all of Australia

[73] Assignee: The Australian National University, Australia

[21] Appl. No.: 38,050

[22] Filed: Mar. 29, 1993

Related U.S. Application Data

[63] Continuation of Ser. No. 656,073, Mar. 6, 1991, abandoned.

[30] Foreign Application Priority Data

Aug. 10, 1988 [AU] Australia ............................. PI9759/88

[51] Int. Cl.⁶ ...................................................... A61K 31/44
[52] U.S. Cl. ............................................................. 514/299
[58] Field of Search .................................................. 514/299

[56] References Cited

U.S. PATENT DOCUMENTS 5,264,356  11/1993  Rohrschneider ........................ 514/299

FOREIGN PATENT DOCUMENTS

WO87/03903  2/1987  WIPO ................................... 514/299

*Primary Examiner*—Jerome D. Goldberg
*Attorney, Agent, or Firm*—Bacon & Thomas

[57] ABSTRACT

A method of anti-inflammatory and/or immunosuppressive treatment of a human or otheer warm-blooded animal patient comprises administration to the patient of an effective amount of castanospermine.

8 Claims, 6 Drawing Sheets

CASTANOSPERMINE AS AN ANTI-INFLAMMATORY AND IMMUNOSUPPRESSANT AGENT

This application is a Continuation of application Ser. No. 07/656,073, filed Mar. 6, 1991, now abandoned.

This invention relates to the use of castanospermine, an alkaloid of the indolizidine class extracted from an Australian native legume, as an anti-inflammatory and immunosuppressant agent.

Castanospermine (CS) is a recently described alkaloid of the indolizidine class, first isolated from the seeds of the Australian legume, *Castanospermum australe* (Hohenschutz et.al, 1981), and has the structural formula:

CS is a potent inhibitor of glucosidase I, which has been shown to inhibit oligosaccharide processing in vitro (Sasak et.al. 1985, Humphries et.al. 1986 and Gross et.al. 1986). The alkaloid also inhibits the enzymes β-glucosidase and β-glucocerebrosidase in vitro (Saul et.al. 1983) and α-glucosidase both in vivo (Saul et.al. 1985) and in vitro (Saul et.al. 1983; Ellmers et.al. 1987 and Chambers and Elbein, 1986).

International Patent Specification WO 8703903, describes the use of glucosidase I inhibitors, preferably castanospermine, as therapeutic agents for combating non-defective retroviral pathogens, including the aetiological agents of AIDS and feline leukaemia. In this specification, the action of the glucosidase I inhibitor is described as interrupting the replication of the retrovirus in infected cells, alleviating pathogenic effects associated with the presentation of vital env glycoproteins on infected cells, and possibly also preventing infection of target cells by interrupting expression of endogenous receptors recognised by the virion.

In addition, European Patent Specification No. 202661 describes the use of a castanospermine-containing composition for the treatment of diabetes, preferably treating postprandial hyperglycaemia or inhibiting carbohydrate absorption in diabetics. In this specification, the activity of castanospermine is described as inhibition of digestive enzymes, thereby reducing the formation of glucose by hydrolysis of complex sugars, as well as inhibition of increased lipid biosynthesis, thereby preventing hyperlipidemia and excessive accumulation of lipids.

In work leading to the present invention, castanospermine has been found to have an inhibitory effect on passively induced experimental allergic encephalomyelitis (EAE) when given in vivo to recipient animals.

Experimental allergic encephalomyelitis is a cell-mediated autoimmune, demyelinating disease of the central nervous sytem (CNS) (Paterson, 1976; Bernard, et.al. 1983). It can be readily induced in a number of animal species by injection of basic protein of myelin (BP) incorporated in complete Freund's adjuvant (CFA). It can also be induced passively by injecting lymphoid cells from CNS antigen sensitized donors into naive syngeneic recipients (Paterson, 1960; Stone, 1961; Levine and Sowinski, 1967). Because of the demyelinating character of EAE it has been used extensively as a model of the human demyelinating disease multiple sclerosis (MS). As a consequence much effort has been directed towards finding ways of inhibiting or suppressing the disease. To this end the most logically relevant studies would be those examining ways to inhibit the effector phase of the disease, i.e. the neuroimmunologic inflammation. Lymphocyte-macrophage interactions are thought to be very important in this inflammatory response. Sensitized lymphocytes, upon entering the CNS, probably recognise specific antigen, i.e. BP, which triggers them to release soluble mediators. These mediators then attract and activate macrophages, which are thought to be the ultimate mediators of demyelination. Inhibition of this process could occur at a number of levels, e.g. blocking lymphocyte-endothelial cell interaction, thereby, preventing entrance of cells into the CNS; inhibition of mediator production/action or inhibition of the activity of the activated macrophages.

Recently, it has been demonstrated that sulphated polysaccharides, such as heparin and fucoidin are powerful inhibitors of the CNS inflammation of EAE (Willenborg and Parish, 1988). This inhibition was not due solely to the anticoagulant activity of these compounds since a heparin preparation devoid of anticoagulant activity also partly inhibited the disease. The precise mechanism of inhibition with these agents is not known but these studies strongly implicate carbohydrate residues in some critical step of the inflammatory process.

Castanospermine has also been found to exhibit an anti-inflammatory effect on passively induced adjuvant arthritis, as well as in actively induced arthritis. Adjuvant-induced arthritis in the rat shares a number of features with arthritis in humans, viz.the presence of a proliferative synovitis and subcutaneous nodules, swelling of extremities, and ultimately cartilage and bone erosion. This animal model has been extensively used for detection of anti-inflammatory and immunosuppressive drugs.

Finally, castanospermine has been found to be effective as an immunosuppressant in preliminary experiments, particularly in preventing tissue graft rejection, and in controlling the delayed hypersensitivity reaction.

In a first aspect, therefore, the present invention relates to the use of castanospermine as an anti-inflammatory and/or immunosuppressive agent. In this aspect, this invention provides a method of anti-inflammatory and/or immunosuppressive treatment of an animal or human patient which comprises administration to the patient of an effective amount of castanospermine.

The effective amount of castanospermine may, for example, comprise from 0.01 to 500 mg/kg/day.

In another aspect, this invention relates to the use of castanospermine in the preparation or manufacture of a pharmaceutical or veterinary composition for anti-inflammatory and/or immunosuppressive treatment. In this aspect, there is provided a pharmaceutical or veterinary composition which comprises castanospermine, together with an acceptable pharmaceutical or veterinary carrier or diluent therefor.

The anti-inflammatory and immunosuppressive effects of castanospermine are further demonstrated in the following Examples.

EXAMPLE 1

Inhibition of EAE by Castanospermine.

a. Materials and Methods

Animals

Female Lewis (RT-1') rats weighing 150 to 200 g were obtained from the Animal Breeding Establishment of the John Curtin School of Medical Research.

Induction of EAE

Guinea pig BP was prepared according to the method of Deibler et.al. (1972) and BP in saline was emulsified in an equal volume of incomplete Freund's adjuvant containing 4 mg/ml added *Mycobacterium butyricum*. Rats received 0.1 ml of emulsion in one footpad of both hind feet. Total dose received was 50 µg of BP and 400 µg of *Mycobacterium butyricum*.

Passive EAE

Cells for passive transfer of EAE were generated following the method of Painitch and McFarlin (1977). Single cell suspensions were prepared from spleens of donor rats sensitized 10–12 days previously with BP-CFA as described above. Cells were cultured at $2 \times 10^6$/ml in RPMI with 5% fetal calf serum (FCS), $5 \times 10^{-5}$M 2-mercaptoethanol, 200 mM L-glutamine and penicillin and streptomycin. Concanavalin A was added at 2 µg/ml and cultures were incubated at 37° in an atomosphere of 10% $CO_2$, 7% $O_2$ and the balance $N_2$. Cells were harvested after 72hrs, washed with Hank's balanced salt solution (HBSS) and transferred to recipient animals via a lateral tail vein. All transfer populations contained $30 \times 10^6$ viable cells.

Evaluation of Clinical EAE

Clinical EAE was graded according to the following scheme: 0-asymptomatic; 1-flaccid distal half of tail; 2-entire tail flaccid; 3-ataxia, difficulty with righting; 4-hindlimb weakness; 5-hindlimb paralysis.

Castanospermine (CS)

Castanospermine was prepared by the method of Hohenschutz et.al. 1981. Because of the anticipated short half-life of CS it was administered in mini-osmotic pumps (Alza model 2ML1) which deliver 10 µl/hr over 7 days. The pumps were implanted subcutaneously in the back of rats and in each experiment control rats were sham operated.

b. Results

Preliminary toxicity studies (data not shown) indicated that CS given at 500 mg/kg/day for 7 days had no apparent toxic effect on animals observed for a 6 week period after treatment. In the first experiment the effect of 100, 200 or 300 mg/kg/day of CS on passively induced EAE was examined. In this experiment the osmotic pumps Containing CS were implanted at the time of cell transfer. Table 1 shows that 300 mg/kg/day gave complete protection against clinical EAE, whereas 200 mg/kg/day afforded only partial protection as seen by a decrease in the mean clinical score. 100 mg/kg/day had no protective effect.

Figure 1A:
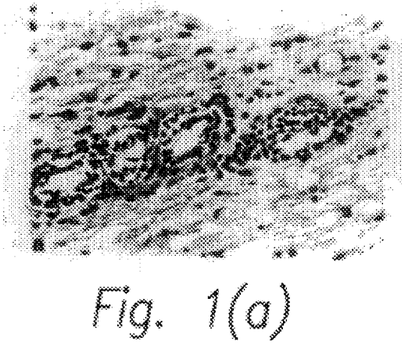
FIGS. 1a–1f, FIGS. 2a–2f, FIG. 3 and FIG. 4 are histological photomicrographs of rat tissue samples.
Figure 1B:
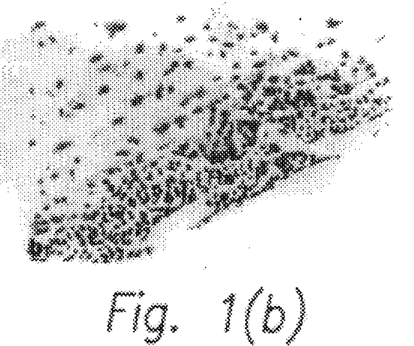
Figure 1C:
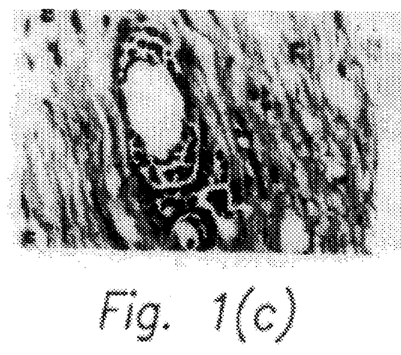
Figure 1D:
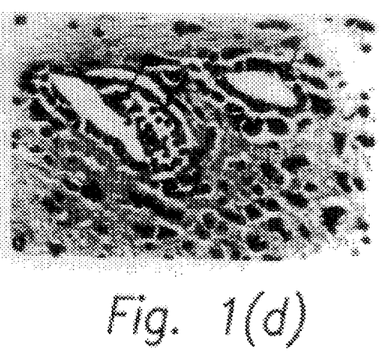
Figure 1E:
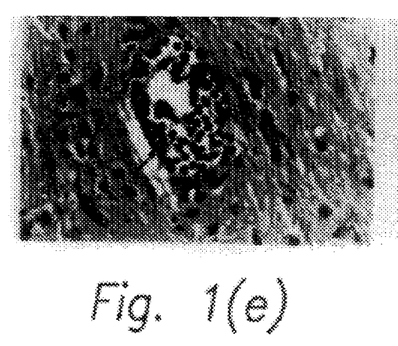
Figure 1F:
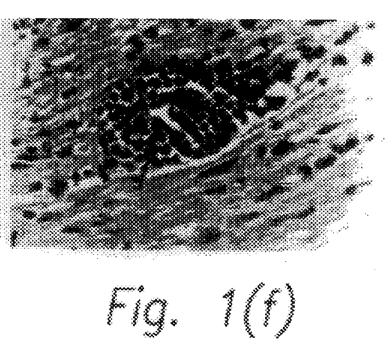
Figure 2A:
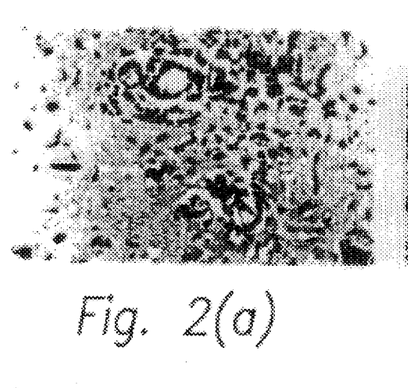
Figure 2B:
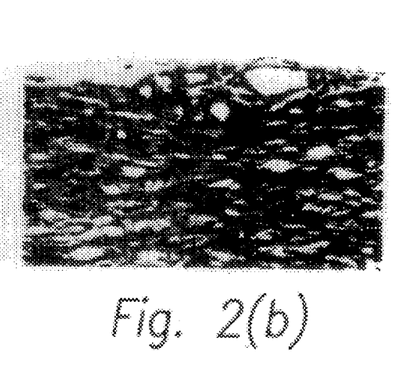
Figure 2C:
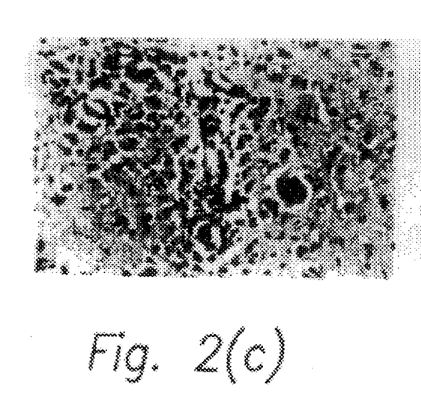
Figure 2D:
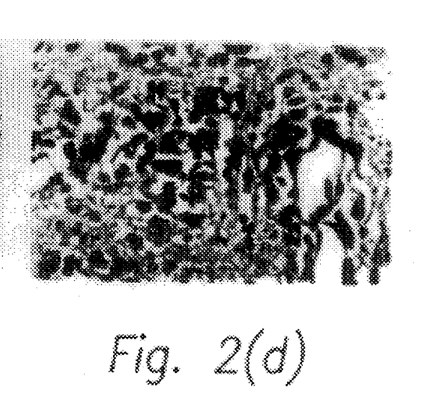
Figure 2E:
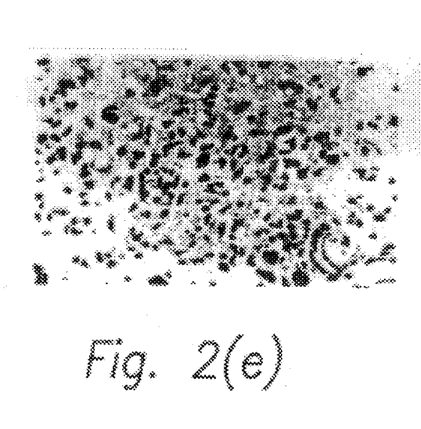
Figure 2F:
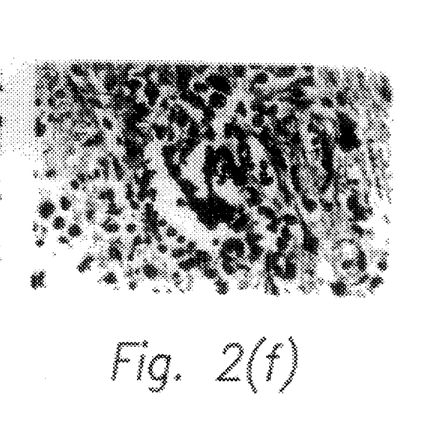
Figure 3:
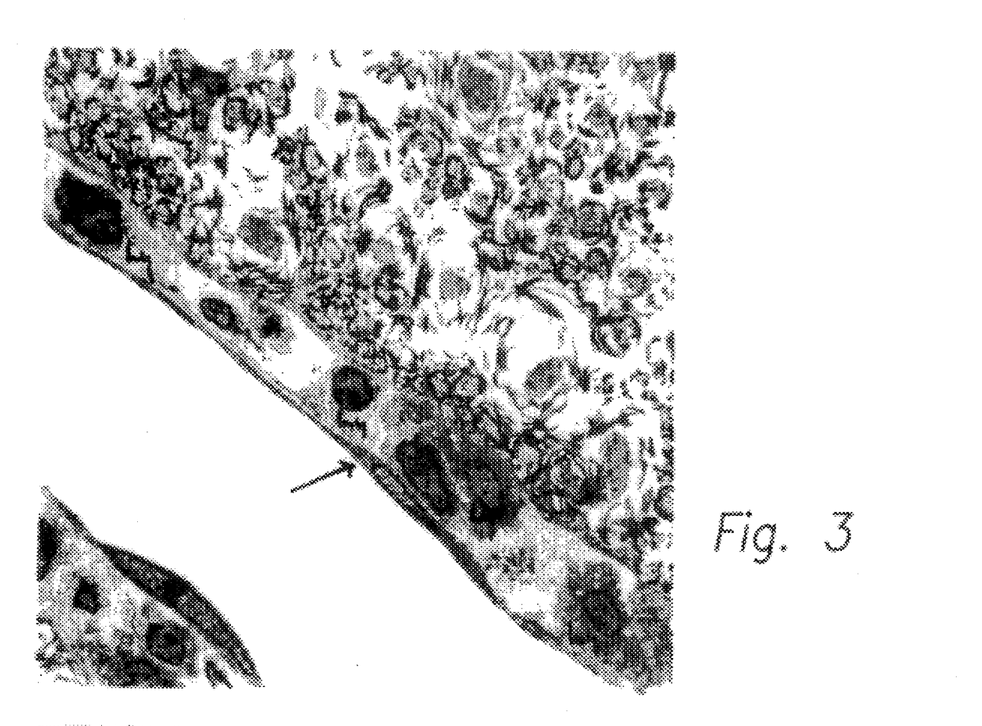
Figure 4:
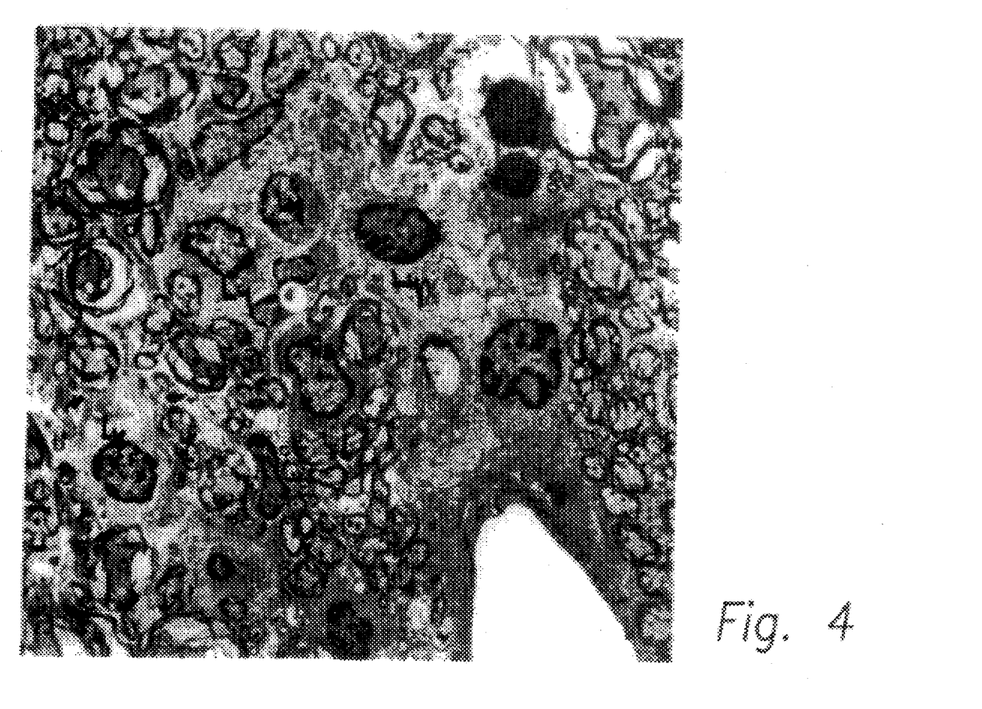

Control rats and those receiving 300 mg/kg/day of CS were killed at day 8 for histological examination of CNS tissues. FIGS. 1a–1f and FIGS. 2a–2f are photomicrographs taken for histological examination, respectively, of a rat treated with CS (300 mg/kg/day) from time of cell transfer to day 7, and a control (untreated) rat. In FIGS. 1a–1f, though no clinical EAE was seen numerous inflammatory lesions were present in the lower spinal cord; a FIGS. 1a and FIGS. 1c–1f show intense, compact perivascular inflammatory lesions. Solid arrows point to endothelium and show that cells have migrated through the endothelium. Broken arrows show some structure possibly responsible for limiting further cell migration into the parenchyma. FIG. 1b shows intense meningitis in treated rat. FIGS. 2a and 2c–2f show diffuse inflammatory lesions. FIG. 2b shows mild meningeal involvement. Treated rats, surprisingly, had approximately the same number of inflammatory lesions as untreated rats, however, the distribution and quality of lesions was different. Treated rats showed intense inflammatory-infiltrates in the meninges of the spinal cord as well as frequent involvement of the root exit and entrance zones. Meningeal involvement in control animals was seen only rarely and when seen was mild. Furthermore, perivascular inflammatory lesions in CS treated rats were often very intense but were compact with inflammatory cells remaining closely marginated around the vessels. In contrast, lesions in control rats were more diffuse with cells migrating away from the vessels and infiltrating extensively into the parenchyma of the spinal cord. The photomicrographs of FIG. 3 shows that in rats which received CS 300 mg/kg/day via osmotic pump beginning at time of EAE cell transfer (no clinical disease observed and animal killed on day 8 for electron microscopy), lymphoid cells (Ly) have crossed the venular endothelium (arrow) but have failed to enter the parenchyma of the brain. In contrast, FIG. 4 shows that in an untreated control rat showing clinical EAE on day 8 after EAE cell transfer, there has been infiltration of lymphoid cells (Ly) into brain parenchyma.

The ability of CS to inhibit passively induced EAE in recipient animals which had an already compromised blood-brain barrier, brought about by a previous episode of passively induced disease, was examined. Rats recovered from one episode of passively induced disease are equally as susceptible to a second challenge as are naive animals (Willenborg 1979; Hinrichs et.al. 1981). When such animals were implanted with a pump delivering CS at 300 mg/kg/day on the day of secondary transfer they did not develop a second episode of the disease (Table 2). The same dose of CS (300 mg/kg) was again shown to protect naive animals from primary disease.

The ability of CS to inhibit disease when treatment was delayed for some days after transfer of the cells was also examined. Two 150 mg/kg injections of CS were given intraperitoneally morning and evening, beginning 4 days after cell transfer and continuing for 3 days. As shown in Table 3 (exp.1) these animals did not develop clinical signs of EAE. When this experiment was repeated however, treated animals were not protected; all developed clinical disease (exp.2; Table 3). Examination of the data showed, however, that in the first experiment disease signs in untreated animals were not apparent until day 6, whereas, in the second experiment all animals had at least minimal signs at the time treatment was begun. it would appear, therefore, that suppression by CS is only effective if treatment is started before onset of disease symptoms. Another possibility is that twice daily injections in the second experiment somehow failed to maintain adequate drug levels. To examine this possibility, an experiment was performed in which osmotic pumps were implanted on day 4 after cell transfer. In this experiment all animals showed mild clinical signs on day 4 and treatment with CS failed to modify subsequent disease expression (exp.3; Table 3), suggesting that treatment must be initiated before onset of clinical signs.

The above results show that the alkaloid castanospermine inhibits passively induced experimental allergic encephalomyelitis in a dose-dependent manner when the drug is given before onset of clinical disease. Histology taken from treated animals provides some insight into the potential mechanism by which CS inhibits EAE. Contrary to what might have been expected from the clinical picture, lesions were found in treated animals. These were characteristically intense but compact, with inflammatory cells tightly packed around the vessels and little migration into the parenchyma in comparison with controls. The cells were clearly able to cross the endothelium but subsequently appeared to accumulate between the endothelium and some presumably limiting structure. The presence of these lesions suggests that CS does not work by inhibiting emigration of lymphocytes from blood across the endothelium but may function by blocking the further penetration of effector cells into the parenchyma of the CNS.

The mechanisms responsible for this activity are not known but based upon previous findings with heparin in passively-induced EAE (Willenborg and Parish, 1988), it is conceivable that CS may be working by inhibiting enzymatic activity needed for effector cell emigration across the vascular endothelium and its underlying basal lamina. CS is known to inhibit specific steps in N-linked oligosaccharide processing necessary for the formation of so-called high mannose structures, which, after phosphorylation, become specific recognition markers of lysosomal enzymes. In the absence of these markers lysosomal enzymes cannot be transported from the rough endoplasmic reticulum/Golgi complex to the lysosomes nor can they be recaptured on the cell surface and internalized as they normally would (von Figura and Hasilik, 1986; West, 1986; Kornfield, 1987). Thus, the overall effect of CS might be to cause depletion or at least functional depletion of enzymes necessary for emigration of EAE effector cells from the venules into the parenchyma of the brain. The ultimate inability of the inflammatory cells to penetrate the parenchyma prevents clinical disease. There are, of course, other possible mechanisms by which CS may be functioning such as the inappropriate glycosylation of cell surface proteins-a process to which the anti-metastatic activity of CS has been attributed (Humphries et.al. 1986).

TABLE 1

Protective effects of CS on passive EAE.

| CS dose[a] mg/kg/day | animals with EAE | mean day of onset | mean[b] clinical score |
|---|---|---|---|
| none | 4/4 | 4 ± 0 | 4.25 ± 0.14 |
| 100 | 4/4 | 4 ± 0 | 4.0 ± 0 |
| 200 | 4/4 | 5 ± 0 | 2.0 ± 0 |
| 300 | 0/4 | — | — |

[a]Drug was delivered in miniosmotic pumps placed subcutaneously at the time of cell transfer.
[b]Mean score out of possible 5 ± standard errors.

TABLE 2

Effect of CS on passive EAE in rats with a compromised blood-brain barrier.

| Rats | CS dose[a] mg/kg/day | animals with EAE | mean[b] clinical score |
|---|---|---|---|
| naive | 0 | 4/4 | 3.75 ± 0.14 |
| naive | 300 | 0/4 | — |
| convalescent | 0 | 4/4 | 4 ± 0 |
| convalescent | 300 | 0/4 | — |

[a]Drug was delivered in miniosmotic pumps placed subcutaneously at the time of cell transfer.
[b]Mean score out of possible 5 ± standard errors.

TABLE 3

Failure of CS to modulate EAE when given after onset of clinical signs.

| experiment number | treatment[a] | animals with EAE | mean[b] clinical score |
|---|---|---|---|
| 1 | saline | 4/4 | 3.5 ± 0.28 |
|   | CS 150 mg/kg i.p., 12 hourly | 0/3 | — |
| 2 | saline | 4/4 | 4 ± 0.2 |
|   | CS 150 mg/kg i.p., 12 hourly | 3/3 | 4 ± 0 |
| 3 | saline | 4/4 | 4 ± 0 |
|   | CS 300 mg/kg osmotic pump | 5/5 | 4 ± 0 |

[a]Treatment initiated on day 4.
[b]Mean score out of possible 5 ± standard errors.

EXAMPLE 2

Effect of Castanospermine on passively induced adjuvant arthritis.

a. Methods (DAxLewis)$F_1$ rats were immunized with 3 mg *M. butyricum* in light mineral oil injected intradermally in both hind feet. Ten days later spleens were removed and made into a single cell suspension in RPMI containing 5% fetal calf serum, 200 mM L Glutamine, $5 \times 10^{-5}$M 2-ME, penicillin and streptomycin. Cells were adjusted to $2 \times 10^6$ cells/ml, and cultured in 50 ml media in 75 mm culture flasks. ConA was added at 2 µg/ml and cultures incubated for 72hrs at 37° C. in an atmosphere of 10% $CO_2$, 7% $O_2$ and the balance $N_2$. Cells were then washed and transferred at $50 \times 10^6$ or $60 \times 10^6$ cells/rat i.v. into 10 weeks old male (DAxLewis)$F_1$.

Castanospermine was put in osmotic pumps (Alza Corp.) which delivered 5 µl/hr for 14 days. Pumps were implanted subcutaneously at the time of cell transfer. Rats received 350mg/kg/day of castanospermine.

b. Results

Hind feet of rats were measured in 4 diameters beginning the day of cell transfer. The measurements are averaged and expressed as % change in volume of feet.

Two experiments have been performed both treating rats with 350 mg/kg/day castanospermine beginning the day of cell transfer. The results are shown in Table 4.

TABLE 4

Effect of CS on passively induced adjuvant arthritis.

| control | % Δ in foot volume | |
|---|---|---|
|  | Day 7 | Day 14 |
| Exp 1 - $50 \times 10^6$ cells | | |
| 1 | +18% | +40% |
| 2 | +22% | +26% |
| 3 | +17% | +32% |
| 4 | +18% | +25% |
| 5 | +16% | +25% |
| CS treated - $50 \times 10^6$ cells | | |
| 1 | +12% | +4% |
| 2 | −5% | −1% |
| 3 | 5% | 0 |
| 4 | 0 | +9% |

TABLE 4-continued

Effect of CS on passively induced adjuvant arthritis.

| control | % Δ in foot volume | |
|---|---|---|
| | Day 7 | Day 14 |
| Exp 2 - 60 × 10⁶ cells | | |
| 1 | +12% | +40% |
| 2 | +31% | +99% |
| 3 | +17% | +77% |
| 4 | +21% | +18% |
| 5 | +28% | +45% |
| CS treated - 60 × 10⁶ cells | | |
| 1 | −5% | −8% |
| 2 | −7% | −18% |
| 3 | −3% | −14% |
| 4 | +3% | −1% |

In no case did any of the CS treated rats show inflammation and only one (#1, Exp 1) showed moderate swelling at a single time period. All rats in experiment 1 were killed for histological examination.

In experiment 2 the osmotic pumps were removed on day 15 and all animals followed out to day 28+. Controls continued to show very significant degrees of swelling and inflammation whereas CS treated rates remained normal; even 2 weeks after drug was discontinued.

EXAMPLE 3

Effect of Castanospermine on passively induced adjuvant arthritis.

In separate experiments to determine the effect of CS on passively induced adjuvant arthritis, the methods of Example 2 were repeated, however the treatment with CS (325 mg/kg/day) was commenced 7 days after injection of cells (60×10⁶ cells/rat).

Figure 5:
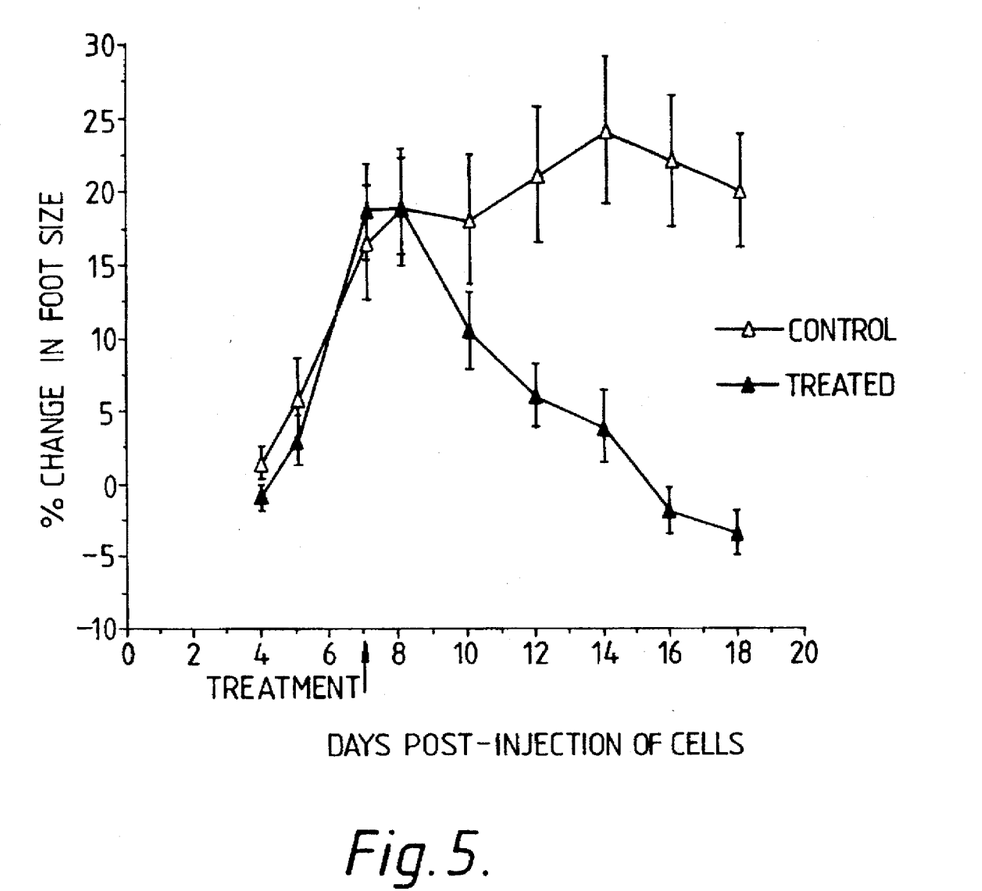
FIGS. 5 and 6 are graphs which show percent change in foot size of treated and control rats.
Figure 6:
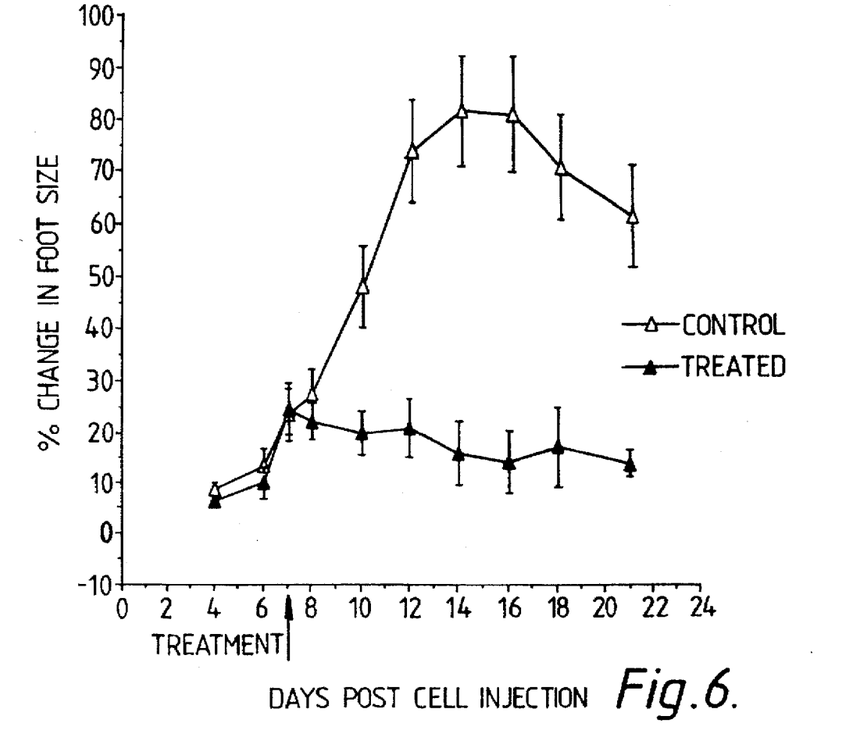

The results of two separate experiments showing % change in foot size of treated and control rats (5 rats/group) are shown graphically in FIGS. 5 and 6.

EXAMPLE 4

Effect of Castanospermine on actively induced arthritis.

Figure 7:
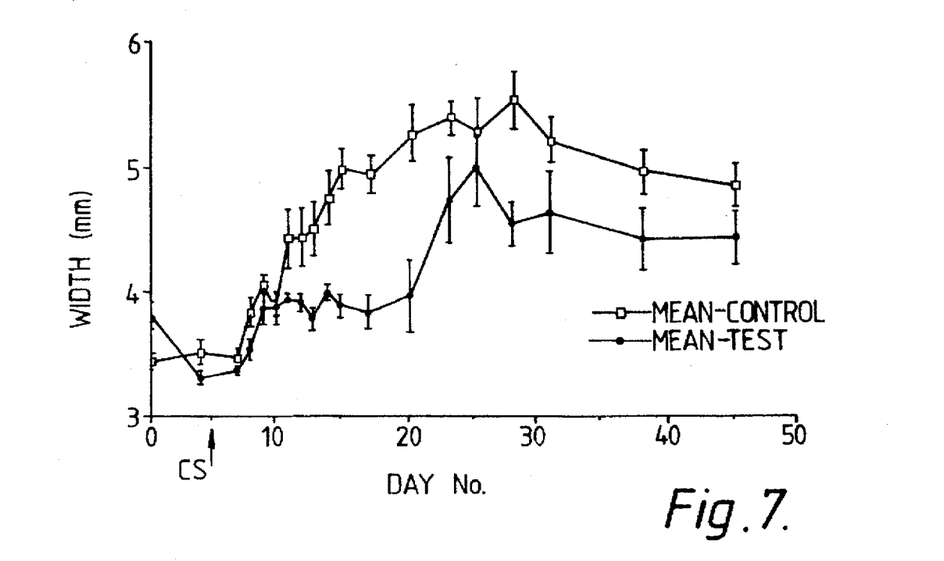
FIGS. 7, 8, and 9 are graphs which show the change in mid foot widths, mean mid foot circumferences and mean ankle widths respectively for control and test groups of rats for a period of 50 days.
Figure 8:
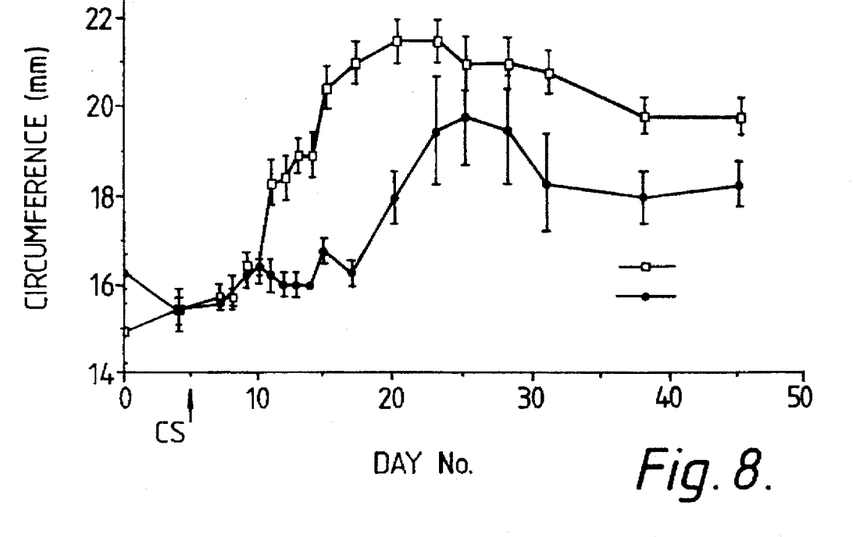
Figure 9:
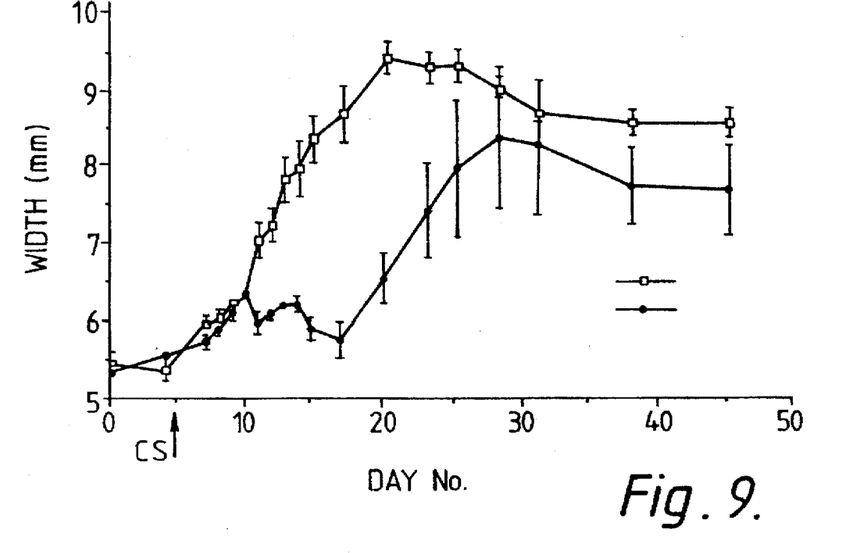

In this example, arthritis was actively induced to rats by the injection of *M.butyricum* in light mineral oil at the base of the tail and at several subcutaneous sites over the lower back. Mid foot and ankle widths were measured over a period of 50 days. Arthritic changes were noticeable after 10 days. Pumps containing 200 mg/kg/day castanospermine were implanted at day 5 after injection of *M.butyricum*. 7 rats were used in both test and control groups. The results in the control and test groups are shown graphically in FIGS. 7, 8 and 9, comparing mid foot widths, mean mid foot circumferences and mean ankle widths, respectively.

EXAMPLE 5

Immunosuppressive effect of Castanospermine in transplantation of pancreatic islets.

a. Methods

Donor mice were Balb/c ($H2^d$) and recipients were CBA ($H2^k$). Donor pancreatic islets were prepared using standard techniques. Approximately 400 islets were isolated from 10 donor mice. These freshly isolated islets, in groups of 50, were placed into CBA blood clots and these were placed under the kidney capsule of CBA mice which were diabetic (blood glucose 20 mM/liter).

Two recipients were implanted (subcutaneously) with miniosmotic pumps containing CS at the time of islet transplantation. These pumps delivered CS at a dose of 300 mg/kg/mouse/day for a period of 14 days. Two control mice were sham operated.

Blood samples (10 μl ) were taken daily and assayed for blood glucose using an automatic analyser (Beckman Glucose Analyzer 2).

b. Results

All transplant recipients became normoglycaemic within 24 hours indicating successful transplantation of all of the grafts. Rejection of grafts was assumed to occur when animals became hyperglycaemic. Control animals rejected on days 9 and 12.

One CS treated mouse did not reject until day 19 five days after the miniosmotic ceased to function. The other CS treated animal rejected on day 12. The reason for this became apparent when the miniosmotic pump was removed and examined and found not to have delivered its CS payload.

EXAMPLE 6

Effect of Castanospermine in renal graft survival.

This example demonstrates graft survival of DA rats receiving renal allografts from fully allogeneic (DA/LEW) donors treated with castanospermine. One kidney from each rat was replaced with a donor kidney, after which the remaining original rat kidney was removed. The results are set out in Table 5 below:

TABLE 5

| Number of Rats | Concentration of Castanospermine | No. of rats surviving more than 14 days | No. of days of Survival |
|---|---|---|---|
| 9 | 100 mg/kg | 1 | 100 |
| 7 | 250 mg/kg | 1 | 33 |
| *5 | no pump | 0 | — |
| **6 DA/DA | no pump | 6 | 100 |

*This control has been performed on many other occasions and no rat has ever survived more than 14 days.
**Syngeneic control.

EXAMPLE 7

Delayed hypersensitivity (DTH): effect of Castanospermine.

C57BL mice were given $10^8$ sheep red blood cells (SRBC) intravenously. Five days later $10^5$ SRBC in a volume of 10 μl was injected into the left hind footpad and 10 μl saline into the right. Castanospermine was given every 4 hours ip beginning at the time of footpad testing. Total dose of CS over 24 hrs was 300 mg/kg/mouse. Control mice were given saline every 4 hours, and 5 mice/group were used in both test and control groups.

In the control group, a 33% increase in foot swelling resulted, whereas the corresponding increase in foot swelling in the test group receiving CS was 11%. REFERENCES:

1. Bernard, C. C. A., P. R. Carnegie and I. R. Mackay (1983), Immunoregulatory mechanisms in experimental autoimmune encephalomyelitis and multiple sclerosis. In: J. F. Hallpike, C. W. Adams and W. W. Tourellotte (Eds.) "Multiple Sclerosis", Chapmen and Hall, London, pp.479–511.
2. Chambers, J. P. and A. D. Elbein (1986), Effects of castanospermine on purified lysosomal alpha-1,4-glucosidase. *Enzyme*, 35:53–56.
3. Deibler, G. E., R. E. Martenson and M. W. Kies (1972), Large scale preparation of myelin basic protein from central nervous tissue of several mammalian species. *Prep. Biochem.*2:139–165.
4. Ellmers, B. R., B. L. Rhinehart and K. M. Robinson (1987). Castanospermine: an apparent tight-binding inhibitor of hepatic lysosomal alpha-glucosidase. *Biochem. Pharmacol.* 36:2381–2385.
5. Figura, K. von and A. Hasilik (1986). Lysosomal enzymes and their receptors. *Ann. Rev. Biochem.* 55:167–193.
6. Gross, V., T. -A. Tran-Thi, R. T. Schwarz, A. D. Elbein, K. Decker and P. C. Heinrich (1986). Diffrent effects of the glucosidase inhibitors 1-deoxynojirimycin, N-methyl-1-deoxynojirimycin and castanospermine on the glycosylation of rat $\alpha_1$-acid glycoprotein. *Biochem. J.* 236:853–860.
7. Hinrichs, D. J., C. M. Roberts and F. J. Waxman (1981). Regulation of paralytic experimental allergic encephalomyelitis in rats: susceptibility to active and passive disease reinduction. *J. Immunol.* 126:1857–1862.
8. Hohenschultz, L. D., E. A. Bell, P. J. Jewess, D. P. Leworthy, R. J. Pryce, E. Arnold and J. Clardy (1981). Castanospermine, a 1,6,7,8-tetrahydroxy-octahydroindolizine alkaloid, from the seeds of *Castanospermum australe. Phytochemistry* 20:811–814.
9. Humphries, M. J., K. Matsumoto, S. L. White and K. Olden (1986). Inhibition of experimental metastasis by castanospermine in mice: blockage of two distinct stages of tumor colonization by oligosaccharide processing inhibitors. *Cancer Res.* 46:5215–5222.
10. Kornfield, S. (1987). Trafficking of lysosomal enzymes. *FASEB Journal* 1:462–468.
11. Levine, S. and R. Sowinski 91968). Passive transfer of allergic adrenalitis and encephalomyelitis with whole blood. *Proc. Soc. Exp. Biol. Med.* 129:221–223.
12. Panitch, H. S. and D. E. McFarlin (1977). Experimental allergic encephalomyelitis: enhancement of cell-mediatd transfer by concanavalin A. *J. Immunol.* 119:1134–1137.
13. Paterson, P. Y. (1960). Transfer of allergic encephalomyelitis in rats by means of lymph node cells. *J. Exp. Med.* 111:119–136.
14. Paterson, P. Y. (1976). Experimental autoimmune (allergic) encephalomyelitis. In: P. A. Miescher and H. J. Muller-Eberhand (Eds.) "Textbook of Immunopathology", Grune and Stratton, New York, pp.179–213.
15. Sasak, V. W., J. M. Ordovas, A. D. Elbein and R. W. Berninger (1985). Castanospermine inhibits flucosidase I and glycoprotein secretion in human hepatoma cells. *Biochem. J.* 232:759–766.
16. Saul, R., J. P. Chambers, R. J. Molyneaux and A. D. Elbein (1983). Castanospermine, a tetrahydroxylated alkaloid that inhibits β-glucosidase and β-glucocerebrosidase. *Arch. Biochem. Biophys.* 221:593–597.
17. Saul, R., J. J. Ghidoni, R. J. Molyneaux and A. D. Elbein (1985). Castanospermine inhibits α-glucosidase activities and alters glycogen distribution in animals. *Proc. Natl. Acad. Sci. USA* 82:93–97.
18. Stone, S. H. (1961). Transfer of allergic encephalomyelitis in rats by means of lymph node cells in inbred guinea pigs. *Science* 134:619–620.
19. West, C. M. (1986). Current ideas on the significance of protein glycosylation. *Mol. Cell. Biochem.* 72:3–20.
20. Willenborg, D. O. (1979). Experimental encephalomyelitis in the Lewis rat: studies on the mechanism of recovery from disease and acquired resistance to reinduction. *J. Immunol.* 123: 1145–1150.
21. Willenborg, D. O. and C. R. Parish (1988). Inhibition of allergic encephalomyelitis in rats by sulfated polysaccharides. *J. Immunol.* 140:3401.

We claim:

1. A method of immunosuppressive treatment of an animal or human patient which comprises blocking the passage of inflammatory cells from the blood stream into the tissues of said patient by the parenteral administration of an effective amount of Castanospermine to the patient in need thereof.

2. A method according to claim 1, wherein said effective amount of castanospermine comprises from 100 to 500 mg/kg/day.

3. A method according to claim 1, wherein said castanospermine is administered to a patient in need of said treatment prior to onset of clinical symptoms requiring immunosuppressive treatment.

4. The method of claim 1 wherein the parenteral administration of the drug is by means of injection.

5. A method of immunosuppressive treatment of an animal or human patient suffering from an autoimmune demyelating disease of the central nervous system which comprises parenteral administration of an effective amount of Castanospermine to said patient suffering from said disease.

6. The method of claim 1 wherein the parenteral administration of the drug is by means of injection.

7. A method of immunosuppressive treatment to inhibit tissue or organ graft rejection in a patient undergoing tissue or organ transplantation, which comprises parenteral administration of an effective amount of Castanospermine to said patient undergoing said organ or tissue transplantation.

8. The method of claim 1 wherein the parenteral administration of the drug is by means of injection.

* * * * *